United States Patent [19]
Eilat et al.

[11] Patent Number: 6,030,997
[45] Date of Patent: Feb. 29, 2000

[54] ACID LABILE PRODRUGS

[76] Inventors: Eran Eilat, 97 Rotschild Blvd., Tel-Aviv 65235; Rina Arad-Yellin, Hayarden 8, Rehovot 76603, both of Israel

[21] Appl. No.: 09/010,030

[22] Filed: Jan. 21, 1998

[51] Int. Cl.[7] .......................... A61K 31/35; C07D 315/00
[52] U.S. Cl. ........................ 514/460; 514/451; 549/417; 549/418; 549/419
[58] Field of Search ................................ 514/451, 459, 514/460, 546, 548; 549/415, 417, 418, 419

[56] References Cited

U.S. PATENT DOCUMENTS

| | | | |
|---|---|---|---|
| 5,087,616 | 2/1992 | Myers et al. | 514/21 |
| 5,094,848 | 3/1992 | Brixner | 424/85.91 |
| 5,140,013 | 8/1992 | Gaudreault et al. | |
| 5,306,809 | 4/1994 | Boon et al. | |
| 5,672,584 | 9/1997 | Borchardt et al. | |

FOREIGN PATENT DOCUMENTS

| | | |
|---|---|---|
| 2131760 | 3/1995 | Canada . |
| 9116920 | 11/1991 | WIPO . |
| 9220702 | 11/1992 | WIPO . |
| 9501369 | 1/1995 | WIPO . |
| 9508556 | 3/1995 | WIPO . |
| 9514706 | 6/1995 | WIPO . |
| 9517403 | 6/1995 | WIPO . |
| 9640709 | 12/1996 | WIPO . |

OTHER PUBLICATIONS

Sieber, P., et al.: 77. Selektive acidolytische Spaltung von Aralkyloxycarbonyl–Aminoschutzgruppen, in *Helv. Chim. Acta.* 51 614–622, 1968.

Nyilas, A., et al.: Arenesulfonylethoxycarbonyl–A Set of Amino Protecting Groups for DNA and RNA Synthesis, in *Nucleosides Nucleotides*, 7 787–793, 1988.

Koole, L.H., et al.: Synthesis of Phosphate Methylated DNA Fragments Using 9–Fluorenylmethoxycarbonyl as Transient Base Protecting Group, in *J. Org. Chem.* 54 1657–1664, 1989.

Wood C.A., et al.: The Influence of Tobramycin Dosage Regimins on Nephrotoxicity, Ototoxicit,y and Antibacterial Efficacy in a Rat Model of Subcutaneous Abscess, in *The Journal of Infectious Disease*, 158:1 13–22, 1988.

Lavie, E., et al.: Monoclonal Antibody L6–daunomycin Conjugates Constructed to Release Free Drug at Lower pH of Tumor Tissue, *Cancer Immunol Immunother.* 33 223–230, 1991.

*Primary Examiner*—Shailendra Kumar
*Attorney, Agent, or Firm*—Skadden, Arps, Slate, Meagher & Flom LLP; Evelyn M. Sommer

[57] ABSTRACT

The invention relates to a pharmaceutically acceptable prodrug which is a covalent conjugate of a pharmacologically active compound and a blocking group, characterized by the presence of a covalent bond which is cleaved at pH values below 7.0. The prodrug may be used in a technique for treating a condition or disease in a mammal related to elevated hydrogen ion concentrations, whereby on administering it to a mammal having such a condition or disease, the pharmacologically active compound is activated selectively within tissues having such elevated hydrogen ion concentrations.

12 Claims, 1 Drawing Sheet

ACID LABILE PRODRUGS

FIELD OF THE INVENTION

The present invention relates to acid labile prodrugs useful in treating a condition or disease that induces a local decrease in pH, and to a technique for treating a condition or disease in a mammal characterized by a localized deviation from the range of physiologically normal pH values.

BACKGROUND OF THE INVENTION

Under normal physiological conditions, the pH of plasma and tissues is maintained at values slightly above neutral pH, in a very narrow range of pH values from approximately 7.38 to 7.42. Some pathological conditions may lead to a systemic decrease in pH such as metabolic acidosis which can be caused by diabetic ketoacidosis, alcoholic ketoacidosis, ketoacidosis due to starvation, poisonings (e.g., methanol, ethylene glycol, salicylates, etc.), severe diarrhea, enzyme defect, and the like. All of these conditions can result in a decrease in systemic pH, although not below pH 7.0, even in severe cases. A similar decrease can be observed in respiratory acidosis that can be caused by decreased ventilation, whether acute or chronic.

In addition to disease conditions that result in a systemic decrease in pH, there are many diseases in humans that produce a localized decrease in pH. These conditions include a wide variety of infectious diseases, as well as many tumors which are related to hypermetabolic activity and/or hypoxic state, all of which are capable of inducing the phenomenon of a localized decrease in normal physiological pH. In localized infectious diseases, the pH can be as low as 4.5, whereas in tumor sites, the pH is 0.7 to 1.0 pH unit lower than normal physiological pH.

All chemotherapeutic agents used to treat cancer are associated with severe side effects and toxicity phenomena, most of which are dose dependent. Most anti-infectious agents also demonstrate dose-dependent adverse side effects and toxicity. Therefore, it would be advantageous to be able to reduce these adverse effects by the use of a prodrug that imparts reduced toxicity to therapeutically active systems. Alternatively, it would also be advantageous to reduce the overall toxic effects of therapeutic agents on a patient's system through minimization of the delivery of the therapeutic, and therefore toxic, component of treatment agents to clinically irrelevant tissue sites.

It would also be advantageous to target diseased tissues characterized by slightly acidic pH values through utilization of a prodrug which could be activated selectively within a range of pH values falling below 7.0. It would thus be possible to introduce a therapeutic system comprising a prodrug with both a pharmacologically active component and an acid-labile linker component into a patient and selectively activate the therapeutic system by decomposing the prodrug and releasing the pharmacologically active component in the target diseased tissues rather than in the healthy cells. In this manner, delivery of the toxic, pharmacologically active component of the prodrug to tissue sites that do not meet the criteria of reduced pH associated with certain disease states, and where the presence of the active component is clinically irrelevant, can be minimized. This has the potential to improve the therapeutic index of the drug, and possibly lower the total dosage necessary to achieve the desired clinical result, thereby reducing the toxic side effects of the pharmacologically active species on the patient's system.

The use of prodrugs to impart desired characteristics such as increased bioavailability or increased site-specificity of known drugs is a recognized concept in the state of the art of pharmaceutical development. The use of various blocking groups, which must be removed in order to release the active drug, is also known in the prior art. Commonly, one or more blocking groups may be attached via an available reactive functional group on the drug. This type of prodrug may be cleaved by nonspecific esterases to effectively release the active principle over a prolonged period of time, in a sustained-release fashion compared to the native drug species. In none of the examples of the use of such a strategy known to the prior art has it been possible to achieve preferential accumulation of the drug within the diseased tissues or organs by activation after exposure to a specific range of pH outside of normal physiological values.

A wide range of blocking groups is known in the art, as compiled, for instance, in the textbook of Greene and Wuts, *Protective Groups in Organic Synthesis*, John Wiley & Sons, Inc.: New York (1991). As disclosed in the prior art, many blocking groups are reactive under strongly acidic conditions, i.e., pH values in the range of 1 to 2. However, only a few are marginally reactive in the range of pH between 4 and 6 (see, for example, ibid., pp. 411–450). Nowhere in this above referenced art is it taught or suggested that a blocking group for an amine or hydroxyl group, for example, can be removed efficiently by exposure to pH values in the range of about 4 to 7.

Acid labile protecting groups have been used also in the laboratory synthesis of nucleic acids and also peptide nucleic acid as disclosed for example in WO 96/40709, WO 94/22802, and WO 93/20090. These disclosures do not relate to the field of drug delivery or prodrug activation.

Acid-labile cis aconitic anhydride derived linker molecules for targeting cytotoxic therapeutic agents such as adriamycin, used in the treatment of cancer, are disclosed in U.S. Pat. No. 5,306,809. These linkers are designed to conjugate the drug to a carrier molecule such as a protein, an antibody or antibody fragment, a polymer, or a nucleic acid in order to provide a targeting system to the vicinity of the cancer cells where the pharmacologically active species of the therapeutic agent is then available to react with target tissue to which it is preferentially delivered on the basis of a property, such as immunospecificity in the case of antibodies, of the carrier molecule.

Conjugates constructed to release free drug at the lower pH of tumor tissue were also disclosed, using monoclonal antibody L6 and daunomycin (Lavie et al., *Cancer Immunol, Immunother.* 33, 223–230, 1991). This targeting system involved a pH sensitive linker of cis aconitic anhydride, which attached the drug to the antibody.

Acid-sensitive spacer molecules used in conjugates constructed to release the free drug at the lower pH of tumor tissue were also disclosed in U.S. Pat. Nos. 4,631,190, 4,997,913 and 5,140,013. This targeting system involved a drug linked to a biopolymer or an antibody via a pH sensitive linker based on cis aconitic anhydride. THe immunospecificity of the antibody segment of the system enables the preferential delivery of the conjugate to the target tissue site. Once there, the decreased pH conditions release the pharmacologically active component, where it then free to react with the tumor tissue.

Other types of prodrugs are known in the art to enable the preferential delivery of a drug to a specific target tissue site, or to be released within a specific organ. This approach is exemplified in the case of the phospholipid prodrugs of salicylates and nonsteroidal anti-inflammatory drugs disclosed in WO 91/16920 which, taken orally, protect the gastric mucosa and release the active drug ingredient in the gut. In other examples of phospholipid prodrugs, formulation of the prodrugs into liposomes or other micellar structures is the feature that enables their preferential uptake, for instance by macrophages, or by liver cells, as in the case of the phospholipid conjugates of antiviral drugs disclosed in WO 90/00555 and WO 93/00910. In other instances, specific types of polar lipids are used to target the prodrugs to intracellular organelles, as in the case of the antiviral and antineoplastic nucleosides disclosed in U.S. Pat. No. 5,149, 794.

A novel esterase-sensitive cyclic prodrug system for peptides that utilizes a trimethyl lock-facilitated lactonization reaction for the release of the peptides has been disclosed in U.S. Pat. No. 5,672,584. This disclosure describes a strategy for preparing cyclic prodrugs of peptides that have increased metabolic stability and increased cell membrane permeability compared to the linear peptide. This strategy involves taking advantage of a predesigned lactonization system. In human plasma, the prodrug releases the original peptide through what is believed to be the esterase-catalyzed hydrolysis of the phenyl ester bond which initiates the lactonization reaction. As a result of this specific reaction, the linear peptide is reformed and released in the target cell. It is neither taught nor suggested in this reference that this type of prodrug species might be activated (converted to the active therapeutic form) by other than esterase catalyzed hydrolysis. The reference is utterly lacking in any teaching or suggestion that acidic pH induced-lactonization could achieve the desired end product of a linear peptide. More importantly, there is no teaching or suggestion in this reference that the specific cyclization scheme might have any utility for drugs other than peptides.

SUMMARY OF THE INVENTION

In accordance with one object of the invention, there are provided prodrugs which selectively undergo activation to release pharmacologically active compounds under conditions of acidic pH. In accordance with another object of the invention, the pharmacologically active compound is released from the prodrug in response to elevated hydrogen ion concentrations in the diseased tissues. In accordance with yet another object of the invention, the pharmacologically active compound selectively accumulates in a tissue characterized by relatively elevated hydrogen ion concentrations therein, and therefore exhibits an enhanced desired activity therein.

The present invention accordingly provides in one aspect, a prodrug which is a conjugate of a pharmacologically active compound and at least one blocking group, characterized by the presence of a covalent bond which is labile in the presence of an elevated concentration of hydrogen ions.

In another aspect, the invention provides pharmaceutical compositions for treating a condition or disease in a mammal related to acidic pH values, by selectively accumulating a pharmacologically active compound within tissues having said acidic pH values, comprising a pharmaceutically acceptable prodrug, which is a conjugate of the pharmacologically active compound and a blocking group, characterized by the presence of a covalent bond which is labile in the presence of elevated hydrogen ion concentrations, such that the bond is cleaved in response to pH values between 4.0 and 7.0.

In yet another aspect, the present invention provides a method for treating a condition or disease in a mammal, related to supranormal hydrogen ion concentrations, which comprises administering to a mammal having such condition or disease, a pharmaceutically acceptable prodrug, the prodrug being a conjugate of a pharmacologically active compound and a blocking group, characterized by the presence of a covalent bond which is labile in the presence of elevated hydrogen ion concentrations, such that the bond is broken in response to pH values between pH 4.0 and 7.0, whereby the pharmacologically active compound accumulates selectively within tissues having pH values below 7.0, or in their immediate environment.

Preferred embodiments according to the present invention are prodrugs of antibiotics and antimicrobials and prodrugs of anti-proliferative agents which are characterized in that they are activated in the presence of pH values between about 4.0 to 7.0.

More preferred embodiments according to the present invention are derivatives of drugs wherein at least one amine or one hydroxyl group is blocked by a blocking group prepared from functionally substituted carboxylic acids having a tertiary substituted gamma carbon and a secondary substituted delta carbon. These substituted carbons create conditions which favor the molecule undergoing cyclization yielding a six-membered cyclic lactone moiety and expelling the free drug under acidic pH conditions. Suitable functional groups on the tertiary substituted carbon may be hydroxy, amine or thiol.

Other preferred embodiments according to the present invention are derivatives of drugs wherein at least one amine or one hydroxyl group is blocked by a blocking group prepared from functionally substituted carboxylic acids having a tertiary substituted beta carbon and a secondary substituted gamma carbon. These substituted carbons create conditions which favor the molecule undergoing cyclization yielding a five membered cyclic lactone moiety and expelling the free drug under acidic pH conditions. Suitable functional groups on the tertiary substituted carbon may be hydroxy, amine or thiol.

Most preferred embodiments according to the present invention are derivatives of drugs wherein at least one amine or one hydroxyl group is blocked by a blocking group prepared from an hydroxycarboxylic acid having a tertiary substituted beta or gamma carbon and a secondary substituted gamma or delta carbon, respectively. These substituted carbons create conditions which favor the molecule undergoing cyclization yielding a five or six membered cyclic lactone moiety and expelling the free drug under acidic pH values in the range of about 4.0 to 7.0. Irrespective of the exact mechanism of the reaction, these blocking groups will undergo cyclization under pH conditions below 7 thereby selectively releasing the active drug species in tissues having a pH value below 7.

Among the currently most preferred embodiments according to the present invention are derivatives of drugs wherein at least one amine or hydroxyl group is blocked by formation of an amide or an ester with 4,4-dimethyl-5-hydroxy-hexanoic acid. Under acidic conditions between the pH values of 4.0 and 7.0, the blocking group in this prodrug will undergo cyclization to form a lactone thereby releasing the free drug species.

An exemplary reaction scheme depicting the release of a drug according to the principles of the present invention is presented in the following schematic representation:

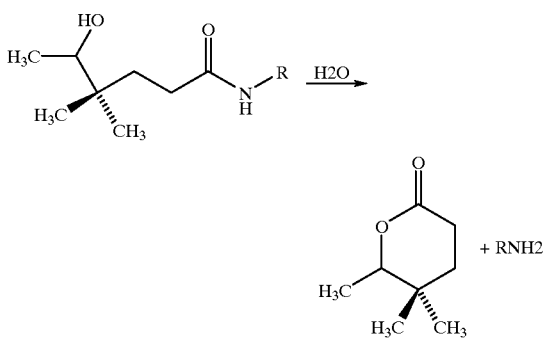

wherein

RNH$_2$ is the pharmacologically active drug species.

Molecules which may serve as acid labile blocking groups or linkers are gamma or delta functionally substituted carboxylic acids that have a tertiary carbon in the beta or gamma position, respectively, according to general Formulae Ia and Ib:

Formula Ia:

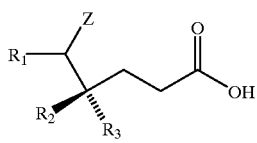

wherein:
R$_1$, R$_2$ and R$_3$ are independently selected from the group consisting of branched or straight chain alkyl groups comprising 1–18 carbon atoms, aryl groups; and, R$_2$ and R$_3$ may be combined to form a cyclic structure;

Z is selected from the group consisting of OH, NHY, and SH; and

Y is selected from the group consisting of H, R$_4$, or NH$_2$; and, wherein R$_4$ is selected from the group of lower alkyl and aryl groups.

Formula Ib:

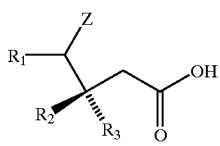

wherein:
R$_1$, R$_2$ and R$_3$ are independently selected from the group consisting of branched or straight chain alkyl groups comprising 1–18 carbon atoms, aryl groups; and, R$_2$ and R$_3$ may be combined to form a cyclic structure;

Z is selected from the group consisting of OH, NHY, and SH; and

Y is selected from the group consisting of H, R$_4$, and NH$_2$; and, wherein R$_4$ is selected from the group of lower alkyl and aryl groups.

The general formulae of derivitized prodrug molecules to which at least one molecule of these novel blocking groups or linkers is bound is depicted in Formulae II and III:

Formula II:

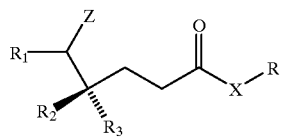

wherein:
RXH denotes a pharmacologically active agent wherein X denotes O or NH;

R$_1$, R$_2$ and R$_3$ are independently selected from the group consisting of branched or straight chain alkyl groups comprising 1–18 carbon atoms, aryl groups; and, R$_2$ and R$_3$ may be combined to form a cyclic structure;

Z is selected from the group consisting of OH, NHY, and SH;

Y is selected from the group consisting of H, R$_4$, or NH$_2$; and wherein R$_4$ is selected from the group of lower alkyl and aryl groups.

Formula III:

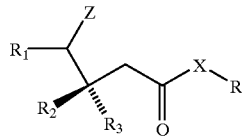

wherein:
RXH denotes a pharmacologically active agent wherein X denotes O or NH;

R$_1$, R$_2$ and R$_3$ are independently selected from the group consisting of branched or straight chain alkyl groups comprising 1–18 carbon atoms, aryl groups; and, R$_2$ and R$_3$ may be combined to form a cyclic structure;

Z is selected from the group consisting of OH, NHY, and SH;

Y is selected from the group consisting of H, R$_4$, or NH$_2$; and, wherein R$_4$ is selected from the group of lower alkyl or aryl groups.

It will be appreciated by the skilled artisan that the reaction rate will vary with the selection of the appropriate substituent on the tertiary center, so that the bulkier the substituents on the beta carbon, the greater the rate of the cyclization reaction under acidic pH values.

A prodrug according to a currently more preferred embodiment of the present invention, wherein the pharmacologically active agent contains at least one hydroxyl group, and the prodrug is an ester thereof having the general formula IV:

Formula IV

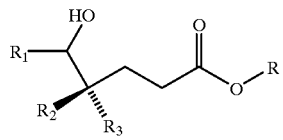

wherein,
ROH denotes a pharmacologically active agent;
R$_1$, R$_2$ and R$_3$ are independently selected from the group consisting of branched or straight chain alkyl groups comprising 1–18 carbon atoms, or aryl groups; or, $R_2$ and $R_3$ may be combined to form a cyclic structure.

A prodrug according to a currently more preferred embodiment of the present invention, wherein the pharmacologically active agent contains at least one amine group, is an amide thereof having the general Formula V:

Formula V

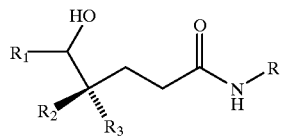

wherein:

$RNH_2$ denotes the pharmacologically active agent; and $R_1$, $R_2$ and $R_3$ are independently selected from the group consisting of branched or straight chain alkyl groups comprising 1–18 carbon atoms; or, $R_2$ and $R_3$ may be combined to form a cyclic structure.

Different classes of pharmacologically active molecules can be administered as prodrugs according to the principles of the present invention. Candidates include, but are not limited to antibiotics and antimicrobials including antifungal agents as well as antibacterial agents (including anti-tuberculosis agents), antitumor drugs, anti-malaria drugs and anti-inflammatory drugs.

It will also be self-evident that the present concept can be applied to the treatment of conditions or diseases other than those related to infectious diseases. By way of example, if the active entity incorporated in the prodrug molecule is an anti-proliferative agent, after administration of the prodrug the inhibitor would be accumulated in or near cells exhibiting abnormal proliferation and lowered pH, thus providing potentially an important tool for use in antitumor therapy. The decreased side effects afforded by the use of the prodrugs according to the present invention would permit use of more efficacious doses.

Non-limiting examples of suitable drugs include:

antifungal compounds as exemplified by amphotericin B and flucytosine;

antibacterial compounds, including the glycopeptides as exemplified by vancomycin and teichoplanin; the beta-lactams as exemplified by ampicillin, ceftriaxon, ceftazidime, cefuroxime, cefaranide, cefoxitin and cefmetazole; the aminoglycosides as exemplified by the compounds gentamicin, kanamycin, tobramycin, netilmicin, streptomycin, amikacin and neomycin; the macrolides as exemplified by clarithromycin and azithromycin; and isoniazid, imipenem and chloramphenicol;

cancer chemotherapeutic agents as exemplified by the compounds bleomycin, methotrexate, mitoxantrone, doxorubicin, daunorubicin, idarubicin, epirubicin, melphalan, dacarbazine, cisplatinum, carboplatin and mithomycin.

A currently most preferred example of such pharmacologically active molecules is the antibiotic gentamicin which suffers from a narrow therapeutic index, the major side effects including nephrotoxicity and ototoxicity that greatly limit its usefulness, and the usefulness of additional aminoglycosides which have excellent anti-infectious action.

DETAILED DESCRIPTION OF THE INVENTION

Figure 1A:
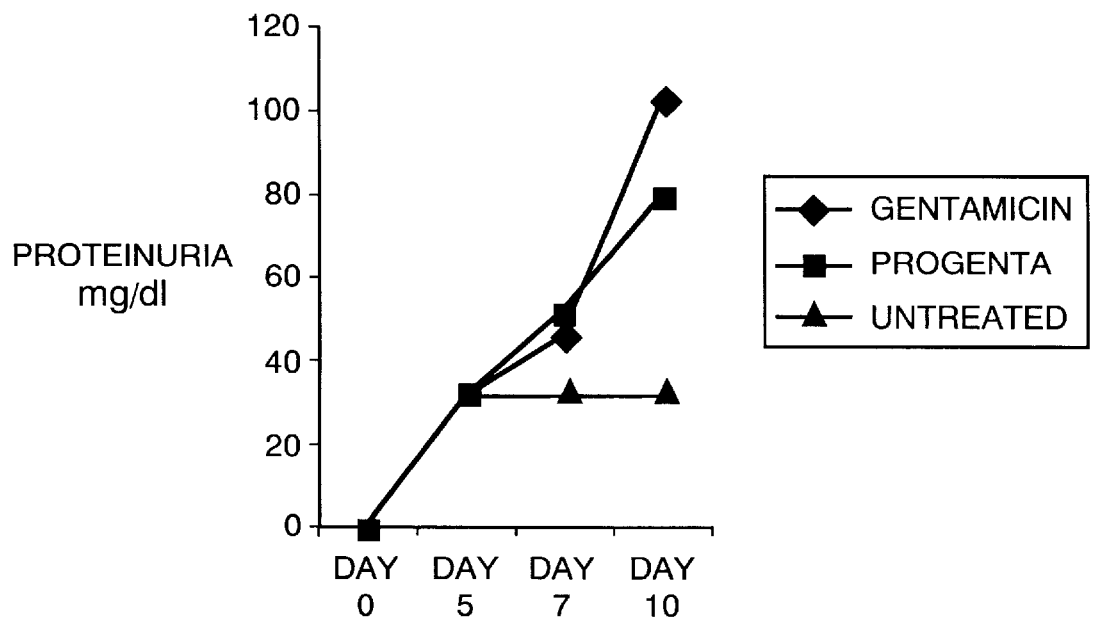
FIG. 1, in two panels, compares renal toxicity of derivitized Gentamicin compared to the native Gentamicin in rats (male Fisher 344 rats in panel 1A; female Fisher 344 rats in panel 1B).

According to the present invention, there is provided a therapeutic system comprising a prodrug with both a pharmacologically active component and an acid-labile linker component covalently bound to at least one binding group of the active drug molecule such that the covalent bond is labile in the presence of elevated concentrations of hydrogen ions. As used herein, the term prodrug denotes a species that is not expected to exert the pharmacological activity of the active compound. Said active compound will exert its therapeutic effects after the prodrugs of the invention undergo acid-facilitated decomposition. The covalent bond of these prodrugs is labile in the presence of pH values below 7.0 that are present in the tissues that are infected, inflamed or malignantly transformed, thereby providing selective activation of the pharmacological compound in the diseased tissues.

In certain preferred embodiments, the pharmacologically active molecule may be a known antibiotic or a known antiproliferative drug. In those embodiments wherein the pharmacological compound is an antibiotic drug, the active compound could be selectively accumulated in the infected tissues.

In other preferred embodiments, the pharmacological agents that are incorporated into the prodrugs of the invention are anti-proliferative agents. In those embodiments, the regulated activation of the active compound is achieved in those tissues or cells that require treatment, thereby significantly improving the therapeutic index of the pharmacological agent.

Various esters or conjugates of drugs that are released or regenerated in vivo have previously been disclosed either a) to enhance penetration into cells; b) to enable sustained or controlled release of drugs; or c) as a means of targeting the drug preferentially to a specific tissue or organ wherein the active species is released by the action of enzyme-catalyzed biochemical processes.

Prodrugs according to the present invention, unlike those disclosed in the prior art, achieve a significantly enhanced therapeutic index provided by selective, acid-facilitated activation of the prodrug in the affected tissues or organs, compared to the advantage of mere sustained or targeted delivery afforded by conventional esters or amides.

The prodrugs according to the present invention can be administered to a patient in need thereof by any of the conventional parenteral routes of administration, as may be appropriate for the disease or condition to be treated. These routes include, but are not limited to, intravenous (i.v.) injection, intramuscular (i.m.) injection, subcutaneous (s.c.) injection, intradermal injections, infusion into a body cavity, cerebrospinal injection, localized infiltration into a target tissue, buccal absorption, oral administration of entero-coated solid dosage forms, topical application and aerosol inhalation, in an amount effective to treat the disease or disorder. Formulations of the compounds of the present invention into pharmaceutical compositions suitable for the chosen route of administration may include any physiologically acceptable solutions, suspensions, emulsions, micro emulsions, micellar dispersions, or the like, with any pharmaceutically acceptable excipients, as are known in the art. In addition, formulations may include various encapsulations or depots designed to achieve sustained release of the prodrug, as in those circumstances where a chronic disorder is to be treated.

Generally, oral administration is not appropriate for the compositions according to the present condition, since the prodrug would be cleaved in the acidic conditions of the stomach. Nevertheless, it may be possible to administer the prodrugs orally in the form of enterocoated tablets or other types of formulation that are designed to prevent the drug from contacting the gastric mucosa, if these prevent the prodrug from being exposed to the acidity of the gastric environment.

According to one preferred embodiment of the present invention, antibiotic drugs are covalently bound to a blocking group which is cleaved in the presence of acidic conditions with a pH between about 4.0 and 7.0.

One non-limiting example of such antibiotics is the drug Gentamicin, which is derivitized to provide a prodrug according to the principles of the present invention, as exemplified herein below.

Persons skilled in the art will appreciate in what manner the concept of the invention may be applied to conditions and diseases which are not necessarily related to an infectious agent, so that in such other cases, the prodrug will incorporate an active compound which is not an antibiotic but which will possess other desired pharmacological activity.

In this connection, it is contemplated that application of the principles of the present invention to anti-proliferative drugs would permit a much higher therapeutic index to be achieved, enabling use of a much more effective dose of these antitumor drugs to be used than is otherwise the case, while potentially substantially reducing the occurrence of undesired side-effects.

Where the drug to be modified has an hydroxyl group, the prodrug may be e.g. an ester thereof, such that the bond is acid labile. Where the drug to be modified contains an amine group (primary or secondary), the prodrug may be an amide thereof.

When selecting the appropriate blocking group for the purposes of the present invention, the skilled person will, of course, take into consideration the necessity to avoid such groups that are likely to give rise to undesirable or toxic products after decomposition to provide the therapeutically active component of the prodrug.

The following examples are to be construed in a non-limitative fashion and represent certain preferred embodiments of the invention. One skilled in the art can readily devise many variations and modifications of the principles disclosed herein without departing from the scope of the invention.

EXAMPLES

Example 1
Synthesis of Partly Modified Gentamicin

The Gentamicin (150 mg) was suspended in benzene (30 ml). 4,4-dimethyl-5-oxo-hexanoylchloride (100 μl dissolved in 2 mL of benzene) was added dropwise from a dropping funnel and the solution was stirred for 12 hours at room temperature.

The solvent was removed in vacuo and the residue was dissolved in water (20 mL). The aqueous solution was extracted with ether (3 25-mL portions).

Sodium borohydride (40 mg) was added to the aqueous solution which was stirred at room temperature for 2 hours. The aqueous solution was extracted with ether and the aqueous layer was separated and lyophilized.

Proton ($^1$H) NMR of the product indicated that the spectrum of the Gentamicin prodrug species differed from the spectrum for unmodified Gentamicin by the addition of some new peaks that originate from the attachment of the linker molecule. Integration of the appropriate signals indicated that one linker molecule was attached via an amide bond per molecule of Gentamicin.

The molecule was dissolved in $D_2O$ (pH=7.0) and its spectrum was taken every 12 hours for 4 days. No change was observed in the spectrum, indicating that the prodrug molecule did not change.

A sample of the compound was dissolved in a buffer solution (pH=6.5) and was checked after 24 hours. A change in the spectrum was observed. The solution was extracted with chloroform and the residue from the organic phase was identified as the lactone 3,3,4-trimethyl pentanilide derived from cyclization of the linker. The NMR spectrum of the residue of the aqueous solution (in $D_2O$) indicated that about 25% of the linker molecules were removed by hydrolysis of the amide bond and release of the Gentamicin. A similar experiment was repeated at pH=6.0. A 40% decomposition was observed after 24 hours. A 10% release was observed after 6 hours.

At more acidic media (pH<1), more than 90% of the linker molecules were removed and the Gentamicin was recovered in less than 10 minutes.

A prodrug, ProGenta, prepared from the antibacterial drug Gentamicin modified with the pH-sensitive linker according to the above procedures has a structure as follows:

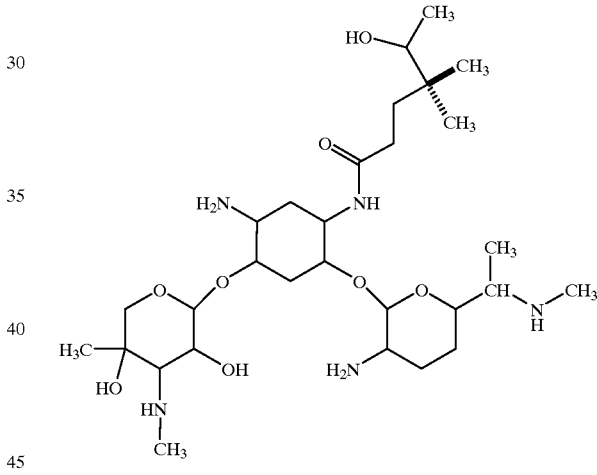

Example 2
Synthesis of Fully Modified Gentamicin

The Gentamicin (150 mg) was suspended in benzene (30 mL). 4,4-dimethyl-5-oxo-hexanoylchloride (400 μL dissolved in benzene) was added dropwise from a dropping funnel and the solution was stirred for 12 hours at room temperature.

The solvent was removed in vacuo and the residue was dissolved in water (20 mL). The aqueous solution was extracted with 3 25-mL portions of diethyl ether.

Sodium borohydride (120 mg) was added to the aqueous solution which was stirred at room temperature for 3 hours. The aqueous solution was extracted with 3 25-mL portions of ether, and the aqueous layer was separated and lyophilized.

Proton ($^1$H) NMR of the product indicated that the spectrum of the Gentamicin prodrug species differed from the spectrum for unmodified Gentamicin by the addition of some new peaks that originate from the attachment of the linker molecule. Integration of the appropriate signals indicated that three linker molecules were attached via amide bonds to one molecule of Gentamicin.

Example 3
Decreased Toxicity of Prodrug of Gentamicin in Rats 3.1 The potential intravenous toxicity of the test article ProGenta (in a dose equimolar to 60 mg/kg of Gentamicin, Example 1) following once daily repeated intravenous administrations during 7 days, was studied in a group of seven male and seven female Fisher 344 rats, in comparison to an identically treated and equally sized group treated with the control article Gentamicin (60 mg/kg), and an untreated control group comprising six male and six female rats. All animals received 10 mg/liter of sodium bicarbonate in drinking water. All animals were allowed an additional 3-day recovery period. Final assessment of treatment effects was based on monitoring clinical signs, determinations of body weight, serum creatinine levels and urinary protein content. In addition, all animals were subjected to necropsy at termination of the study. Damage to the kidney basement membrane will cause excretion of proteins (proteinuria), this damage can be to the tubulus (tubular proteinuria) or to the glomerulus (glomerular proteinuria). Decrease in the Glomerular Filtration Rate (GFR) will result in increased blood level of creatinine.

3.2 No unusual clinical signs evident of toxicity were detected in all test animals throughout the entire study period. One female animal of the ProGenta treatment group died on Day-5 and this was attributed to accidental death at the time of dosing. In the two groups treated with either the test article ProGenta or the control article Gentamicin, a relative reduction in normally expected weight gain was particularly evident among female rats. The drop in body weight gain of these animals in comparison to untreated controls, was especially striking on the third day of the recovery period (Day 10 of the study), suggesting that 'recovery' from treatment was apparently incomplete.

Figure 1B:
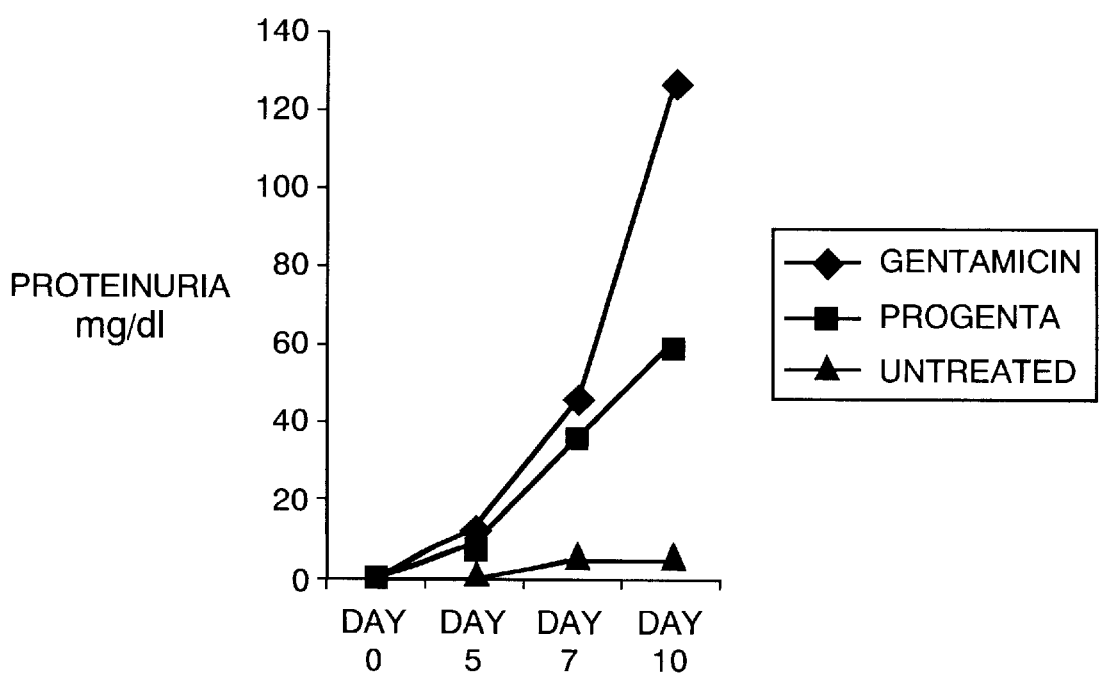

3.3 Serum creatinine revealed no particular differences among the various test groups. On the other hand, determinations of urinary protein content showed that under conditions of this study, determination of changes in urine protein concentration probably was the preferred mechanism for comparative assessment of treatment effects due to its strong correlation to recognized toxicity phenomena, ease of performance, and accuracy. Thus, protein content markedly increased in male (FIG. 1$a$) and female (FIG. 1$b$) rats of both treatment groups on the last day of the daily repeated dosing (Day-7), as compared to that of controls. Furthermore, on the last of the 3-day Recovery Period, proteinuria detected in males and females of the Control Article (Gentamicin) treatment group reached a peak value and exceeded by about 30 and 110 mg/dL, respectively, values of Test Article (ProGenta) treated rats.

The occurrence of both peak creatinine and urinary protein content values on Day-10 suggests that extension of the Recovery Period may possibly provide more meaningful information as to differential effects in response to treatment of the test articles under investigation.

At the end of the experiment, animals were sacrificed and their kidneys were sectioned and stained with Hematoxylin—Eosin staining, and were evaluated in a blind fashion by a Toxicological pathologist. Findings showed decreased toxicity of ProGenta, as observed in the following tables:

TABLE 1

Histopathological findings in kidneys of rats treated with ProGenta - males

| Histological findings | Animal #1 | Animal #2 | Animal #3 | Animal #4 | Animal #5 | Animal #6 | Animal #7 |
|---|---|---|---|---|---|---|---|
| Cortex - tubular basophilia | 2 | 1 | 1 | 1 | 1 | 3 | 1 |
| Cortex- Interstitial mononuclear cell infiltration | 1 | 1 | 1 | 1 | 1 | 2 | 1 |

Key for grading (applicable for all tables):
0 - No remarkable change
1 - Minimal change
2 - Mild change
3 - Moderate change
4 - Marked change

TABLE 2

Histopathological findings in kidneys of rats treated with Progenta Females

| Histological findings | Animal #8 | Animal #9 | Animal #10 | Animal #11 | Animal #12 | Animal #13 | Animal #14 |
|---|---|---|---|---|---|---|---|
| Cortex - tubular basophilia | 1 | 2 | 2 | 1 | 1 | 0 | 1 |
| Cortex- Interstitial mononuclear cell infiltration | 1 | 2 | 1 | 1 | 1 | 1 | 1 |
| Medulla - mineralization | 0 | 0 | 1 | 0 | 1 | 0 | 1 |

TABLE 3

Histopathological findings in kidneys of rats treated with Gentamicin - males

| Histological findings | Animal #15 | Animal #16 | Animal #17 | Animal #18 | Animal #19 | Animal #20 | Animal #21 |
|---|---|---|---|---|---|---|---|
| Cortex - tubular basophilia | 1 | 1 | 2 | 3 | 2 | 2 | 3 |
| Cortex- Interstitial mononuclear cell infiltration | 1 | 1 | 1 | 2 | 2 | 1 | 2 |

TABLE 4

Histopathological findings in kidneys of rats treated with Gentamicin Females

| Histological findings[1] | Animal #22 | Animal #23 | Animal #24 | Animal #25 | Animal #26 | Animal #27 | Animal #28 |
|---|---|---|---|---|---|---|---|
| Cortex - tubular basophilia | 3 | 3 | 3 | 2 | 1 | 1 | 2 |
| Cortex- Interstitial mononuclear cell infiltration | 2 | 1 | 2 | 2 | 1 | 1 | 1 |

TABLE 5

Histopathological findings in kidneys of rats untreated - males

| Histological findings | Animal # 29 | Animal # 30 | Animal # 31 | Animal # 32 | Animal # 33 | Animal # 34 |
|---|---|---|---|---|---|---|
| Cortex - tubular basophilia | 1 | 0 | 0 | 0 | 0 | 1 |
| Cortex - Interstitial mononuclear cell infiltration | 0 | 0 | 0 | 0 | 0 | 1 |

TABLE 6

Histopathological findings in kidneys of rats untreated - Females

| Histological findings | Animal # 35 | Animal # 36 | Animal # 37 | Animal # 38 | Animal # 39 | Animal # 40 |
|---|---|---|---|---|---|---|
| Cortex - tubular basophilia | 0 | 1 | 1 | 1 | 0 | 0 |
| Cortex - Interstitial mononuclear cell infiltration | 0 | 0 | 0 | 0 | 0 | 0 |
| Medulla - mineralization | 0 | 0 | 0 | 0 | 0 | 0 |

3.4 No treatment-related gross abnormalities were detected in any of the test animals.

3.5 In view of the results obtained under the experimental design conditions of this study, it may be concluded that although the Test Article ProGenta obviously compromised normal renal function, it was clearly less than that observed in response to treatment with the Control Article Gentamicin.

Example 4
Decreased Toxicity of Prodrug of Gentamicin in Mice

Four female BALB/c mice were divided into two groups, one group received daily injections of Gentamicin intravenously, at the dose that is reported as LD50 for mice (75 mg/kg i.v.), the second group received an equivalent amount on a molar basis of ProGenta (the prodrug of Example 2. On day 2, the mice in the Gentamicin group showed remarked proteinuria (as measured by Dipstick) whereas the ProGenta treated group showed only slight proteinuria. On day 3, the two mice in the Gentamicin group died several hours after the injection.

The mice in the ProGenta group received two additional rising dosages, one of 150 and one of 200 mg/kg i.v. on days 4 and 5, respectively, and appeared normal with slight proteinuria. Animals were sacrificed on day 7, with no gross pathological findings.

Example 5
Efficacy of ProGenta in Rats and Mice 50 animals (Fisher 344 rats, or mice i.e. BALB/c) divided into 6 groups:

Group 1: 5 animals untreated controls.

Group 2: In 10 animals induction of pseudomonas aeruginosa infected abscess (as described in Wood et al. *J. Infec. Dis.* 158, pp. 13–22 (1988)) and treatment with 30 mg/kg Gentamicin bid.

Group 3: In 10 animals induction of pseudomonas aeruginosa infected abscess and treatment with 30 mg/kg ProGenta bid.

Group 4: In 10 animals induction of pseudomonas aeruginosa infected abscess and treatment with 60 mg/kg Gentamicin bid.

Group 5: In 10 animals induction of pseudomonas aeruginosa infected abscess and treatment with 60 mg/kg ProGenta bid.

Group 6: In 5 animals induction of infected abscess with no further treatment.

In all groups the treatment is continued for 14 days, with injection of the antibiotic in isotonic aqueous solution at physiological pH administered subcutaneously. All animals receive 10 mg/liter of sodium bi- carbonate in drinking water.

Outcome measures determined:

Proteinuria, creatinine in serum, abscess microbiology (as described in Wood et al. *J. Infec. Dis.* 158, pp. 13–22 (1988)), in vivo DNA synthesis (as described in Wood et al., ibid.), renal pathology, and renal antibiotic histology.

Example 6
Prodrugs of Potential Application in the Treatment of Tumors

Introduction

In this Example, there are presented a number of illustrative embodiments of the present invention in which a prodrug comprises an antineoplastic or anti-proliferative drug. After administration of the prodrug, the active drug would be released in or near the tissue which has acidified as a result of hyper-metabolic activity associated with the malignant tissue, thus providing potentially an important tool for use in antitumor therapy.

The anticancer drug Daunomycin modified with the pH sensitive linker:

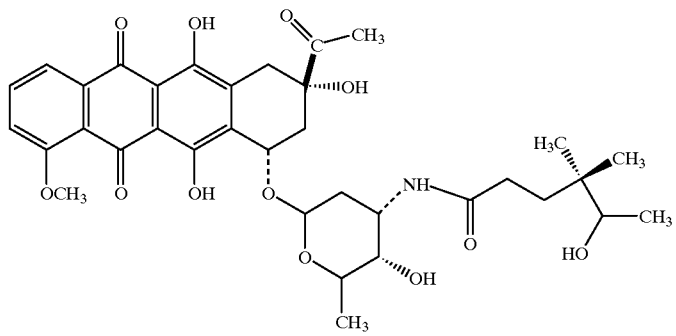

The anticancer drug Mitoxantrone (Novantrone) modified with the pH sensitive linker:

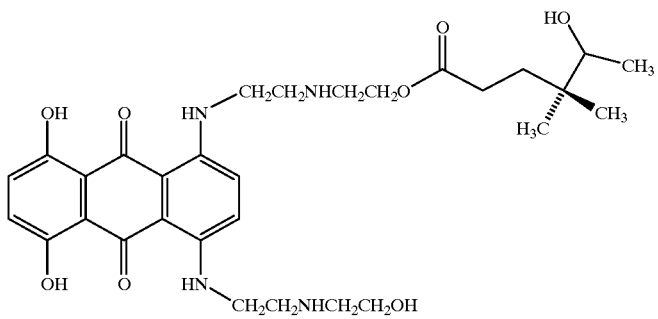

Example 7
Assay to Assess ProDaunomycin and Daunomycin

Cells: Lung carcinoma line (i.e. L-2981), and colon carcinoma line (i.e. C-3347) are maintained in tissue culture flasks in incomplete modified Dulbecco's medium (IMDM) supplemented with 15% heat inactivated fetal calf serum in 37° C. in humidified atmosphere containing 5% $CO_2$.

Cytotoxicity Evaluation

1. Thymidine uptake assay—cells are plated in 96 well plates ($10^6$ cells/well) and incubated overnight. After washing the plates twice with IMDM, the Daunomycin or ProDaunomycin are added. This is followed by a 1 h incubation (5 h are also possible). Subsequently, the cells are washed twice, pulsed with 20 μL of tritiated thymidine, and incubated at 37° C. for 4 h. The plates are then frozen at −20° C., thawed and harvested. The filters are counted in beta counter. The percentage inhibition is calculated as the decrease in uptake of tritium in treated and untreated cells on a log scale.

2. Colonogenic assay—suspended cells are counted and divided into aliquots in test tubes at $10^6$ cells in 1 mL/well. This is followed by removal of the samples, washing, and counting of cells exposed only to medium, to evaluate the number of cells lost by procedure. The concentration of the remaining cells is adjusted accordingly, after which these cells are poured into liquid 3% agar in IMDM, which is layered on top of solid 3% agar placed in 24-well plates. The plates are incubated for 10 days and the numbers of colonies are determined. A colony is defined as a cluster of ten or more cells. The Prodrug is exposed to low pH (6) for 24 or 48 h, without the cells, after which the pH is adjusted to 7.2. Then the mixture is applied to the cells. As controls samples of a ProDaunomycin or Daunomycin are used that were incubated at neutral pH for the same period of time before being added to the cells.

The expected results in the cytotoxic evaluation and the colonogenic assay would be that the ProDaumycin would show percent inhibition of no less than the inhibition shown by the unmodified Daunomycin at a pH of 6.0.

We claim:

1. A pharmaceutically acceptable prodrug that is a covalent conjugate of a pharmacologically active compound and at least one blocking group, wherein the covalent bond is reactively labile at a pH value between pH 4.0 and 7.0, having the general formula:

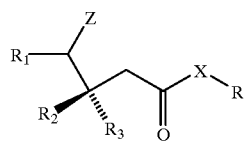

wherein,
   RX-denotes a pharmacologically active agent;
   X is selected from the group consisting of O and NH;
   $R_1$, $R_2$ and $R_3$ are independently selected from the group consisting of branched or straight chain alkyl groups comprising 1–18 carbon atoms, aryl groups; and
   $R_2$ and $R_3$ may be combined to form a cyclic structure;
   Z is selected from the group consisting of OH, NHY, and SH; and
   Y is selected from the group consisting of H, $R_4$, or $NH_2$, wherein $R_4$ is selected from the group of lower alkyl and aryl groups.

2. A pharmaceutically acceptable prodrug that is a covalent conjugate of a pharmacologically active compound and at least one blocking group, wherein the covalent bond is reactively labile at a pH value between pH 4.0 and 7.0, having the general formula:

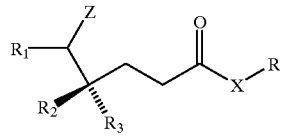

wherein,
   RX-denotes a pharmacologically active agent;
   X is selected from the group consisting of O and NH;
   $R_1$, $R_2$ and $R_3$ are independently selected from the group consisting of branched or straight chain alkyl groups comprising 1–18 carbon atoms, and aryl groups; and, $R_2$ and $R_3$ may be combined to form a cyclic structure;
   Z is selected from the group consisting of OH, NHY, and SH; and
   Y is selected from the group consisting of H, $R_4$, or $NH_2$, wherein $R_4$ is selected from the group of lower alkyl and aryl groups.

3. A prodrug according to claim 2, wherein the pharmacologically active agent contains at least one hydroxyl group, and the prodrug is an ester thereof having the general formula:

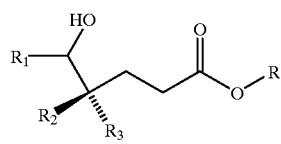

wherein,
   RO-denotes a moiety derived from ROH, pharmacologically active agent; $R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure.

4. A prodrug according to claim 2, wherein the pharmacologically active agent contains at least one amine group, and the prodrug is an amide thereof having the general formula:

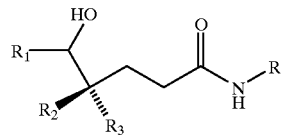

wherein:
   RNH-denotes a moiety derived from $RNH_2$, the pharmacologically active agent; and $R_1$, $R_2$ and $R_3$ are independently selected from the group consisting of branched or straight chain alkyl groups comprising 1–18 carbon atoms; and, $R_2$ and $R_3$ may be combined to form a cyclic structure.

5. A pharmaceutical composition of matter comprising a pharmaceutically acceptable prodrug which is a conjugate of a pharmacologically active compound and at least one blocking group, characterized by the presence of a covalent bond between the blocking group and the active compound that is cleaved at pH values between 4.0 and 7.0, having the general formula:

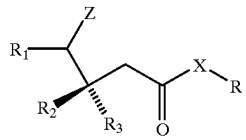

wherein,
   RX-denotes a pharmacologically active agent;
   X is selected from the group consisting of O and NH;
   $R_1$, $R_2$ and $R_3$ are independently selected from the group consisting of branched or straight chain alkyl groups comprising 1–18 carbon atoms, aryl groups; and,
   $R_2$ and $R_3$ may be combined to form a cyclic structure;
   Z is selected from the group consisting of OH, NHY, and SH; and
   Y is selected from the group consisting of H, $R_4$, or $NH_2$, wherein $R_4$ is selected from the group of lower alkyl and aryl groups.

6. A pharmaceutical composition of matter comprising a pharmaceutically acceptable prodrug which is a conjugate of a pharmacologically active compound and at least one blocking group, characterized by the presence of a covalent bond between the blocking group and the active compound that is cleaved at pH values between 4.0 and 7.0, having the general formula:

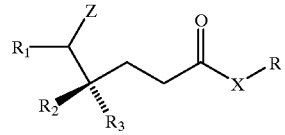

wherein,
   RX-denotes a pharmacologically active agent;
   X is selected from the group consisting of O and NH;
   $R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure;

Z is selected from the group consisting of OH, NHY, and SH; and

Y is selected from the group consisting of H, $R_4$, or $NH_2$, wherein $R_4$ is selected from the group of lower alkyl and aryl groups.

7. A pharmaceutical composition of matter according to claim 5, wherein the pharmacologically active agent contains at least one hydroxyl group, and the prodrug is an ester thereof having the general formula:

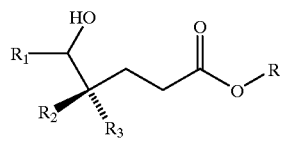

wherein:
RO-denotes a moiety derived from ROH, the pharmacologically active agent agent; and
$R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure.

8. A pharmaceutical composition of matter according to claim 5, wherein the pharmacologically active compound contains at least one amine group, and the prodrug is an amide thereof having the general formula:

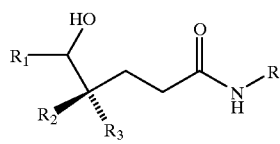

wherein:
$RNH_2$ denotes a moiety derived from RNH2, the pharmacologically active agent; and
$R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure.

9. A method for treating a condition or disease in a mammal related to elevated hydrogen ion concentration, which comprises administering to a mammal having such condition a pharmaceutically acceptable prodrug, said prodrug being a covalent conjugate of a pharmacologically active compound and a blocking group, wherein the covalent bond is reactively labile at a pH value between pH 4.0 and 7.0, having the general formula:

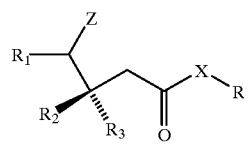

wherein,
RX-denotes a pharmacologically active agent;
X is selected from the group consisting of O and NH;
$R_1$, $R_2$ and $R_3$ are independently selected from the group consisting of branched or straight chain alkyl groups comprising 1–18 carbon atoms, aryl groups; and,
$R_2$ and $R_3$ may be combined to form a cyclic structure;
Z is selected from the group consisting of OH, NHY, and SH; and Y is selected from the group consisting of H, $R_4$, or $NH_2$, wherein $R_4$ is selected from the group of lower alkyl and aryl groups.

10. The method according to claim 9, wherein the prodrug is a covalent conjugate of a pharmacologically active compound and a blocking group, wherein the covalent bond is reactively labile at a pH value between pH 4.0 and 7.0, having the general formula:

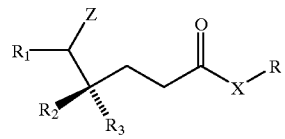

wherein,
RXH denotes a pharmacologically active agent;
X is selected from the group consisting of O and NH;
$R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure;
Z is selected from the group consisting of OH, NHY, and SH; and
Y is selected from the group consisting of H, $R_4$, or $NH_2$, wherein $R_4$ is selected from the group of lower alkyl or aryl groups.

11. The technique according to claim 10, wherein the pharmacologically active agent contains at least one hydroxyl group, and the prodrug is an ester thereof having the general formula:

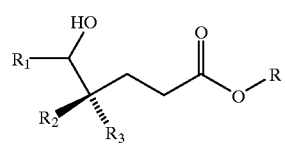

wherein:
ROH denotes a moiety derived from $RNH_2$, the pharmacologically active agent; and
$R_1$, $R_2$ and R 3 are independently selected from the group consisting of branched or straight chain alkyl groups comprising 1–18 carbon atoms, aryl groups; and, $R_2$ and $R_3$ may be combined to form a cyclic structure.

12. The method according to claim 10, wherein the pharmacologically active compound contains at least one amine group, and the prodrug is an amide thereof having the general formula:

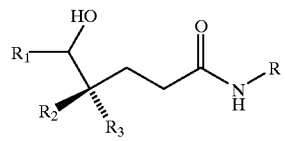

wherein:
RNH-denotes a moiety derived from $RNH_2$, the pharmacologically active agent; and
$R_1$, $R_2$ and $R_3$ are independently selected from the group consisting of branched or straight chain alkyl groups comprising 1–18 carbon atoms, aryl groups; and, $R_2$ and $R_3$ may be combined to form a cyclic structure.

* * * * *